United States Patent [19]

Hoff

[11] Patent Number: 5,406,340
[45] Date of Patent: Apr. 11, 1995

[54] INFANT-TO-TODDLER EYE WEAR INCLUDING HEAD STRAPS

[76] Inventor: Leslie J. Hoff, 11405 S. Oak Dr., Delton, Mich. 49046

[21] Appl. No.: 86,171

[22] Filed: Jun. 30, 1993

[51] Int. Cl.⁶ .................................................. G03C 3/00
[52] U.S. Cl. ..................................... 351/156; 351/155; 2/452
[58] Field of Search ............... 351/156, 155, 158, 157, 351/142, 123; 2/10, 426, 452

[56] References Cited

U.S. PATENT DOCUMENTS

| | | | |
|---|---|---|---|
| 589,307 | 8/1897 | Seffer. | |
| 1,370,806 | 3/1921 | Garner | 351/155 |
| 2,504,524 | 4/1950 | Hayward | 351/156 |
| 3,378,851 | 4/1968 | McBrayer | 2/14 |
| 3,531,187 | 9/1970 | Brown | 351/155 |
| 4,122,847 | 10/1978 | Craig | 128/132 |
| 4,162,542 | 7/1979 | Frank | 2/15 |
| 4,286,340 | 9/1981 | Lathrop | 2/452 |
| 4,411,263 | 10/1983 | Cook | 128/132 |
| 4,502,476 | 3/1985 | Welt | 128/132 |
| 4,520,510 | 6/1985 | Daigle | 2/452 |
| 4,790,031 | 12/1988 | Duerer | 2/15 |
| 5,042,094 | 8/1991 | Sadowsky | 2/439 |

Primary Examiner—William L. Sikes
Assistant Examiner—Hung Xuan Dang

[57] ABSTRACT

Eye wear for a child from infant to toddler wherein the eye wear comprises first and second resilient frames disposed about respective first and second eye lenses. The first and second frames include a flexible, adjustable nose bridge therebetween adapted to engage the bridge of the child's nose and first and second outer frame loops extending from the respective first and second frames toward and stopping short of the child's ears. First and second temple straps are provided each having one end looped about the respective first and second outer frame loops and an opposite end forming respective first and second strap loops. The eye wear includes first and second head straps extending through the respective first and second strap loops to hold the frames on the child's face. The first and second head straps have lower strap portions for extending about the posterior of the child's head and upper strap portions for extending over the child's head forwardly of the soft spot of the child's head. The lower strap portions are fastenable in adjustable overlapped relation behind the child's head and the upper strap are fastenable in adjustable overlapped relation on the child's head.

9 Claims, 3 Drawing Sheets

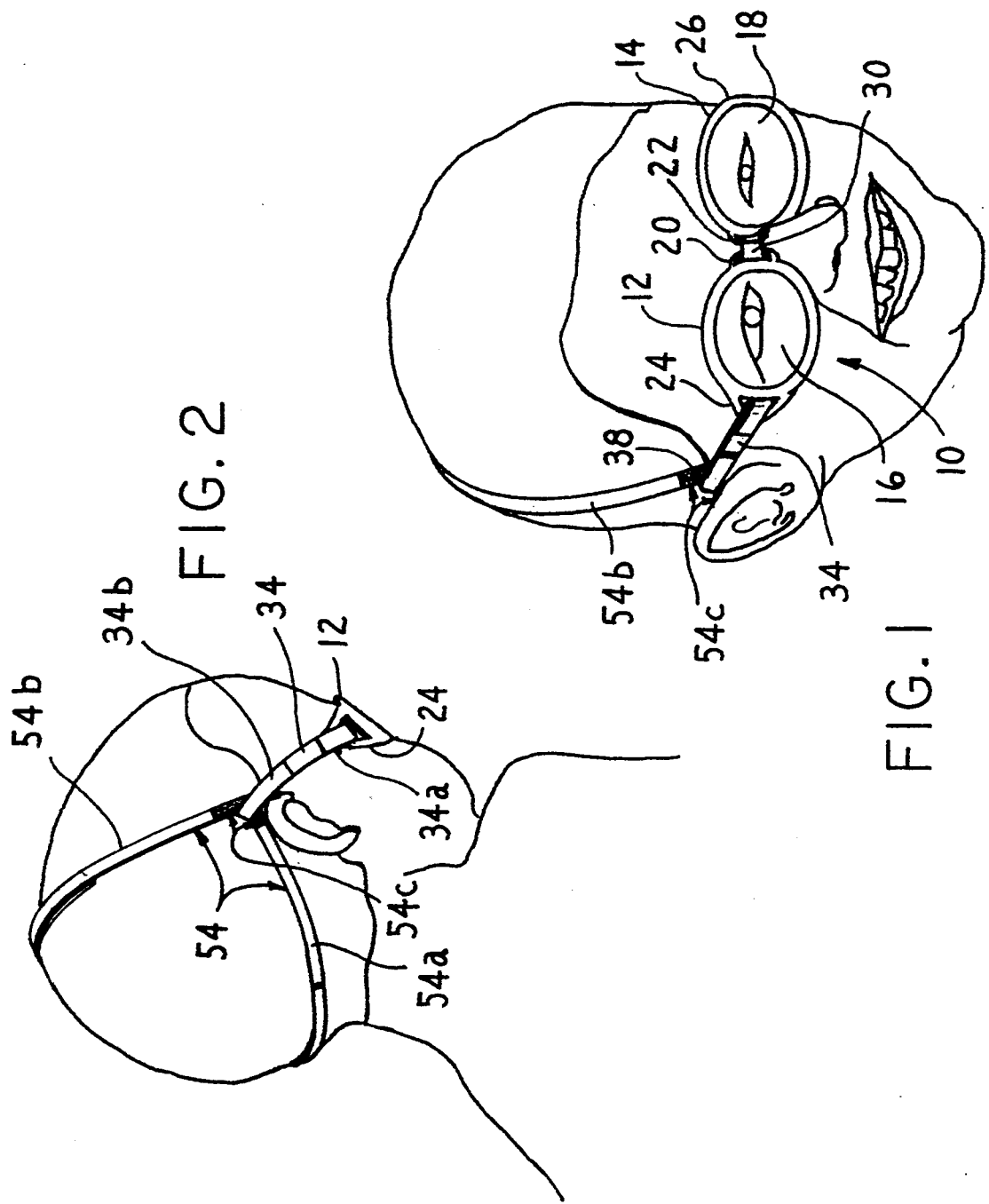

INFANT-TO-TODDLER EYE WEAR INCLUDING HEAD STRAPS

FIELD OF THE INVENTION

The present invention relates to children's eye wear that can accommodate and adjust to changes in the shape and size of the child's head and face over time and that is soft and washable to provide a comfortable fit and needed cleanliness over time.

BACKGROUND OF THE INVENTION

Conventional eye wear used by adults is generally unsuitable for infants and toddlers as a result of the latter's different facial and head features and size that remain to be developed over time to adulthood. For example, the rigid frame of conventional eyeglasses includes a nose bow or bridge adapted to rest on the nose of the wearer and temple pieces hinged to the frame and extending rearwardly over the ears on opposite sides of the wearer's head. The child's nose and ears are generally too small to support the nose bow or bridge and the temple pieces of conventional eyeglasses. Moreover, conventional rigid frame eyeglasses are unable to accommodate the change in shape and size of the child's head and face occurring during the infant-to-toddler stage of growth. In general, as a result, conventional eyeglasses are deficient in their ability to remain in an appropriate position on the child's head during the infant-to-toddler stage of the child's life, It is an object of the invention to provide infant-to-toddler eye wear that comprises lens frame and head strap features that accommodate and adjust to changes in the shape and size of the child's head and face over time. It is another object of the invention to provide infant-to-toddler eye wear that comprises lens frame and head strap features that are soft and washable to provide a comfortable fit and needed cleanliness over time.

SUMMARY OF THE INVENTION

The present invention provides eye wear for a child from infant to toddler wherein the eye wear comprises first and second resilient frames disposed about respective first and second eye lenses. The first and second frames include a flexible nose bridge therebetween adapted to engage the bridge of the child's nose and permit the lens frames to conform to the child's face about the eyes and first and second outer frame loops extending from the respective first and second frames toward and stopping short of the child's ears. First and second temple straps are provided each having one end looped about the respective first and second outer frame loops and an opposite end forming respective first and second strap loops.

The eye wear includes first and second head straps extending through the respective first and second strap loops to hold the frames on the child's face. The first and second head straps have lower strap portions for extending about the posterior of the child's head and upper strap portions for extending over the child's head forwardly of the soft spot of the child's head. The lower strap portions are fastenable in adjustable overlapped relation behind the child's head and the upper strap are fastenable in adjustable overlapped relation on the child's head. The first and second head straps each preferably include an elastic region for holding the frames under tension on the child's race when the lower and upper head strap portions are fastened, whereby the lens frames can angularly conform to the face of the child about the flexible nose bridge.

In a preferred embodiment of the invention, the first and second frames, the temple straps, and the head straps comprise a resilient porous material covered with cloth; e.g. foam rubber covered with terry cloth. This construction is soft, perspiration absorbent, and washable to provide a comfortable fit and cleanliness over time.

The present invention also provides eye wear for a child from infant to toddler wherein first and second resilient frames are disposed about respective first and second eye lenses and include first and second eyelets at inner sides. An adjustable, flexible strap extends through the frame eyelets for interconnecting the first and second frames and is adapted to engage the bridge of the child's nose. Head strap means is connected to the first and second frames at outer sides thereof for holding the frames on the child's face. The head strap means includes lower strap portions for extending about the posterior of the child's head and upper strap portions for extending over the child's head forwardly of the soft spot of the child's head. The lower strap portions are fastenable in adjustable overlapped relation behind the child's head and the upper strap portions are fastenable in adjustable overlapped relation on the child's head.

In a preferred embodiment of the invention, the nose bridge comprises a Velcro strap extending through the first and second eyelets. The Velcro strap is overlapped to adjust the nose bridge to the nose size of the child. The Velcro strap is flexible to permit the lenses frames to be angularly disposed so as to conform to the child's face about the eyes in a manner similar to goggles.

The eye wear of the invention is advantageous in that changes in shape and size of the child's head and face during the infant to toddler stage of growth can be readily accommodated by adjustments to the nose bridge and the upper and lower head strap portions. Moreover, the lens frame and head strap components are soft, perspiration absorbent, and washable to provide a comfortable fit and needed cleanliness over time.

The aforementioned and other objects and advantages of the invention will become more readily apparent from the following detailed description of the invention taken with the following drawings.

BRIEF DESCRIPTION OF THE DRAWINGS

FIG. 1 is a perspective view of eye wear in accordance with one embodiment of the invention shown positioned on an infant's head taken from the front and side of the toddler's head.

FIG. 2 is a perspective view of the eye wear taken from the rear and side of the toddlet's head.

DETAILED DESCRIPTION

Figure 3:
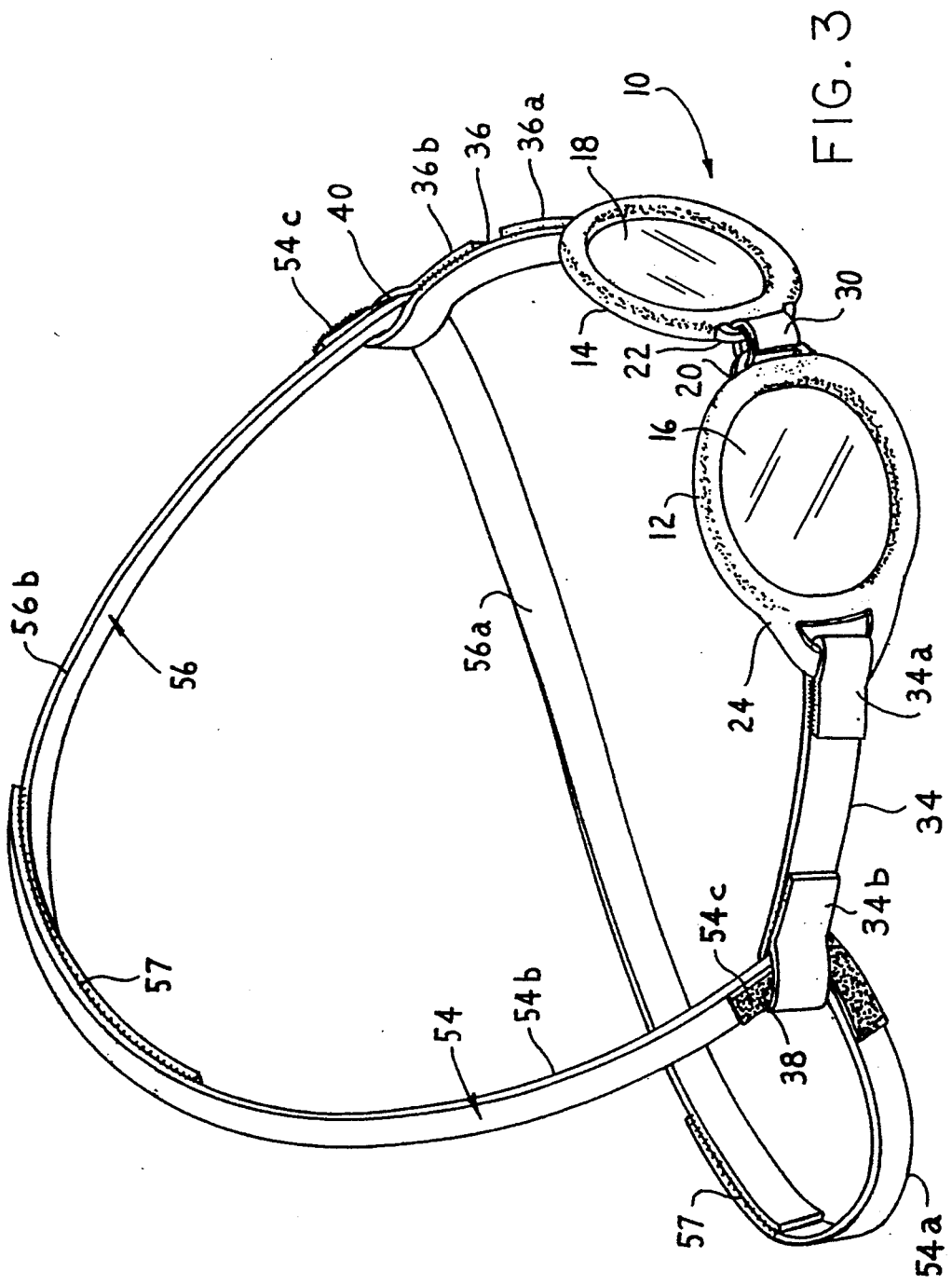
FIG. 3 is a perspective view of the eye wear of FIG. 1 showing the adjustable nose bridge interconnecting the first and second frames.

FIGS. 1-3 illustrate eye wear 10 for a child from infant to toddler and possibly beyond in accordance with one embodiment of the invention. The eye wear 10 comprises first and second soft, resilient, pliable frames 12, 14 disposed about respective first and second eye lenses 16, 18. The eye lenses 16, 18 can be made of conventional shatterproof, relatively rigid plastic lens material. The lenses may be transparent, protective lenses, asethetically colored lenses, light sensitive lenses, or dark lenses for the purpose of protecting the child's sensitive eyes from physical harm and light damage. The lenses 16, 18 comprise the only relatively rigid or hard component of the eye wear 10.

To this end, the lenses 16, 18 are housed or supported in the soft, resilient, pliable first and second frames 12, 14. The first and second frames include first and second eyelets 20, 22 at inner sides and identical first and second integral, outer frame loops 24, 26 at outer sides thereof.

The first and second frames 12, 14 are made of a resilient porous material covered with a soft, perspiration absorbing cloth. For example, the frames 12, 14 can be made of foam rubber or padding covered with terry cloth. This frame construction provides softness, perspiration absorbency, and washability to provide a comfortable fit and cleanliness over the time the eye wear is in use. The frames can be molded in-situ about the lenses 16, 18 or fastened thereto by adhesive or other fastening techniques, such as mechanically joining the frames 12, 14 and the respective lenses 16, 18 via threads (not shown) passing through suitable holes formed in the lenses 16, 18.

The size and shape of the lenses 16, 18 and thus the frames 12, 14 can be varied as desired to provide different eye wear aesthetics. The lenses shape can be selected as desired for asethetic purposes. For example, exaggerated rectangular, circular, and other shapes appealling to children can be used. Moreover, the covering cloth over the frames 12, 14 and other components of the eye wear to be described can be varied to this same end.

The eyelets 20, 22 may each comprise a generally rectangular plastic strap snapped or pressed into the cloth fabric on the frames 12, 14 or into the frames themselves to form the attached loop-like eyelets. The frame loops 24, 26 are made integral with the frames 12, 14 by molding the foam rubber to a suitable shape having the loop features and covering the molded rubber with cloth.

The frames 16, 18 are interconnected at the inner sides by a flexible, adjustable nose bridge strap 30 that extends through the frame eyelets 20, 22. The strap 30 is adapted to engage the bridge of the child's nose and conform thereto as a result of it flexibility. The strap 30 preferably comprises a Velcro strap extending through the first and second eyelets 20, 22. The Velcro strap 30 is overlapped onto itself as necessary to adjust to the nose shape and size of the child. Moreover, the Velcro strap 30 is flexible to permit the lenses frames 12, 14 to conform to the child's face about the eyes in a manner similar to goggles. In particular, the flexible nose bridge strap 30 can permit the lenses frames 12, 14 and lenses therein to be angularly disposed relative to a flat plane so as to conform to the child's face about the eyes.

As shown best in FIGS. 1-2, the first and second outer frame loops 24, 26 extend from the outer sides of the respective first and second frames 16, 18 toward and stopping short of the child's ears. The first and second frame loops 24, 26 are connected to respective first and second temple straps 34, 36 that extend toward and above the ears of the child.

The first and second temple straps 34, 36 each have one end 24a, 36a looped about the respective first and second outer frame loops 24, 26 and an opposite end 34b, 36b forming respective first and second strap loops 38, 40. The first and second temple straps each comprise molded foam rubber or similar resilient material covered by terry cloth or similar soft, perspiration absorbing material. The temple straps 34, 36 each include an elastic region (not shown) formed by elastic strip material joined to the molded foam rubber by sewing and other fastening techniques.

The ends 34a, 36a of the temple straps 34, 36 extend through the respective frame loops 24, 26 and reverse back upon themselves to provide overlapped ends. The ends 34a, 36a include Velcro material thereon in a manner that the reversed back ends are fastened together by the Velcro fasteners.

Similarly, the ends 34b, 36b of the temple straps 34, 36 are reversed back upon themselves to provide overlapped ends to form the aforementioned first and second strap loops 38, 40. The ends 34b, 36b of the temple straps 34, 36 include Velcro material thereon in manner that the reversed back ends 34b, 36b are fastened together by the Velcro fasteners.

The eye wear 10 includes first and second head straps 54, 56 extending through the respective first and second strap loops 38, 40 to hold the frames on the child's face. The first and second head straps 54, 56 have lower strap portions 54a, 56a for extending about the posterior of the child's head and upper strap portions 54b, 56b for extending over the child's head forwardly of the soft spot of the child's head as shown best in FIGS. 1-2. The head straps 54, 56 are individual one-piece construction each comprising molded foam rubber or similar resilient material covered by terry cloth or similar soft, perspiration absorbing material. The head straps 54, 56 each include an intermediate meshing region 54c, 56c comprising Velcro material to mesh with the Velcro material of the strap loops 38, 40 to prevent slippage between the head straps 54, 56 and respective head strap loops 38, 40.

The head straps 54, 56 comprise molded foam rubber or similar resilient material covered by terry cloth or similar soft, perspiration absorbing material. The head straps 54, 56 each include an elastic region (not shown) formed by elastic strip material joined to the molded foam rubber by sewing thread and other fastening techniques. This construction is soft, perspiration absorbent, and washable to provide a comfortable fit and cleanliness over time.

The lower strap portions 54a, 56a are fastenable in adjustable overlapped relation behind the child's head and the upper strap portions 54b, 56b are fastenable in adjustable overlapped relation on the child's head. In particular, the overlapped strap portions 54a, 56a and 54b, 56b include Velcro material 57 or snaps (not shown) thereon in order to permit adjustment of the head straps 54, 56 to accommodate the change in size and shape of the child's head as the child progresses from infant to toddler. The eye wear 10 thus can be used over an extended time as the child develops.

Figure 4:
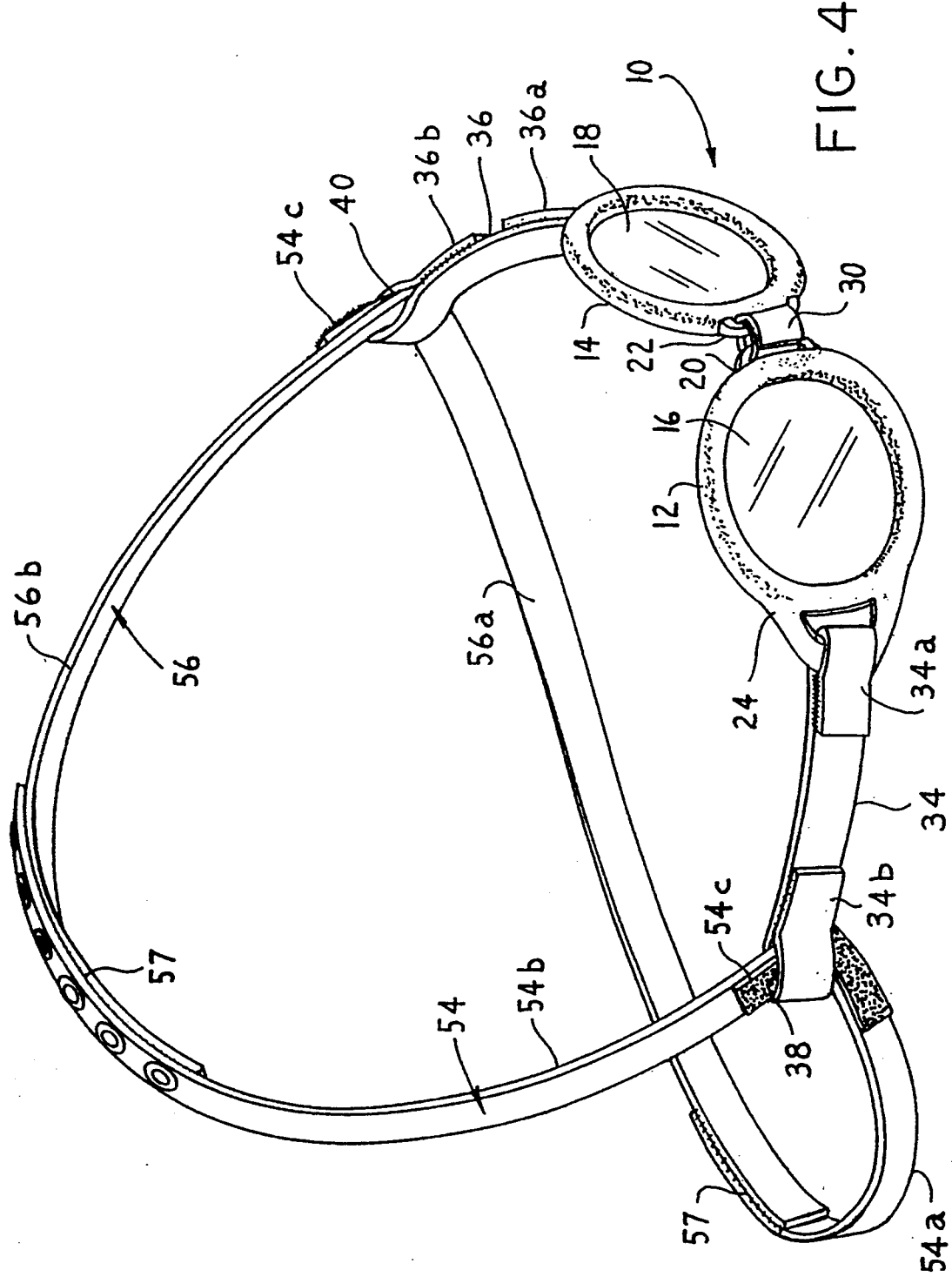
FIG. 4 is similar to FIG. 3 showing soft snap fasteners for the head straps.

As shown in FIG. 4, soft plastic snaps 59 can be provided on the overlapping ends or the head straps 54, 56 in lieu of the Velcro material 57 to fasten the lower strap portions and upper strap portions in adjustable overlapped relation.

The elastic regions in the temple straps and head straps hold the frames 12, 14 under tension on the child's face when the lower and upper head strap portions are fastened, whereby the lens frames can angularly conform to the face of the child about the flexible nose bridge 30.

The head straps 54, 56 extend about the lower posterior and top of the child's head so that the back of the head can rest against a chair or seat back without a strap being in the way. Moreover, the upper strap portions 54b, 56b extend in front of the soft spot present on the infant's head initially so as not to press thereon.

The eye wear of the invention is advantageous in that changes in shape and size of the child's head and face during the infant to toddler stage of growth can be readily accommodated by adjustments to the nose bridge and the upper and lower head strap portions. Moreover, the lens frame and head strap components are soft, perspiration absorbent, and washable to provide a comfortable fit and needed cleanliness over time.

While certain specific and preferred embodiments of the invention have been described in detail hereabove, those skilled in the art will recognize that various modifications and changes can be made therein within the scope of the invention as set forth in the appended claims.

The embodiments of the invention in which an exclusive property or privilege is claimed are defined as follows:

1. Eye wear for a child from infant to toddler, comprising:

first and second cloth-covered resilient frames disposed about respective first and second eye lenses for contacting the child's face, said first and second frames including a flexible nose bridge therebetween adapted to engage the bridge of the child's nose and first and second outer frame loops extending from the respective first and second frames toward and stopping short of the child's ears, first and second cloth-covered temple straps each having one end looped about the respective first and second outer frame loops and an opposite end forming a respective first and second strap loop, said first and second strap loops including meshing material on the inner periphery of each loop, and first and second cloth-covered head straps extending through the respective first and second strap loops to hold the frames on the child's face, said first and second head straps including meshing material at intermediate regions thereof extending through said first and second strap loops for intermeshing with the meshing material on the inner periphery of the respective first and second strap loops, said first and second head straps having lower strap portions for extending about the posterior of the child's head and upper strap portions for extending over the child's head forwardly of the soft spot of the child's head, said lower strap portions having overlapped regions with intermeshing material so as to be fastenable in adjustable overlapped relation behind the child's head and said upper strap portions having overlapped regions with intermeshing material so as to be fastenable in adjustable overlapped relation on the child's head.

2. The eye wear of claim 1 wherein said ends of the first and second temple straps extend through the respective first and second frame loops and reverse back upon themselves to provide overlapped ends.

3. The eye wear of claim 2 wherein the reversed back ends are fastened together by velcro fastener means.

4. The eye wear of claim 1 wherein said opposite ends of the first and second temple straps reverse back upon themselves to form said first and second strap loops.

5. The eye wear of claim 1 wherein the nose bridge of said frame is adjustable in width.

6. The eye wear of claim 5 wherein the nose bridge comprises an overlapped flexible strap extending through first and second eyelets formed on the respective first and second frames.

7. Eye wear for a child from infant to toddler, comprising:

first and second cloth-covered resilient frames disposed about respective first and second eye lenses for contacting the child's face, said first and second frames including first and second eyelets at inner sides and an adjustable strap having overlapped regions with intermeshing material so as to adjustably interconnect the first and second frames and adapted to engage the bridge of the child's nose, and cloth-covered head strap means connected to the first and second frames at outer sides thereof for holding the frames on the child's face, said head strap means including lower strap portions for extending about the posterior of the child's head and upper strap portions for extending over the child's head forwardly of the soft spot of the child's head, said lower strap portions having overlapped regions With intermeshing material so as to be fastenable in adjustable overlapped relation behind the child's head and said upper strap portions having overlapped regions with intermeshing material so as to be fastenable in adjustable overlapped relation on the child's head.

8. The eye wear of claim 7 wherein the nose bridge comprises a flexible strap extending through the first and second eyelets.

9. Eye wear for a child from infant to toddler, comprising:

first and second cloth-covered resilient frames disposed about respective first and second eye lenses for contacting the child's face, said first and second frames including a flexible nose bridge therebetween adapted to engage the bridge of the child's nose and first and second outer frame loops extending from the respective first and second frames toward the child's ears, first and second cloth-covered temple straps each having one end looped about the respective first and second outer frame loops and an opposite end forming a respective first and second strap loop, and cloth-covered head strap means between the first and second strap loops for holding the frames on the child's face.

* * * * *